(12) United States Patent
MacDonald et al.

(10) Patent No.: US 9,815,058 B2
(45) Date of Patent: Nov. 14, 2017

(54) FRACTIONATION OF PARTICLES

(75) Inventors: Michael Peter MacDonald, St Andrews (GB); Kishan Dholakia, St Andrews (GB); Steven Leonard Neale, St Andrews (GB); Gabriel Cooper Spalding, Bloomington, IL (US)

(73) Assignee: The University Court of the University of St Andrews, St Andrews (GB)

( * ) Notice: Subject to any disclaimer, the term of this patent is extended or adjusted under 35 U.S.C. 154(b) by 1476 days.

(21) Appl. No.: 10/554,937

(22) PCT Filed: May 7, 2004

(86) PCT No.: PCT/GB2004/001993
§ 371 (c)(1),
(2), (4) Date: Dec. 13, 2006

(87) PCT Pub. No.: WO2004/100175
PCT Pub. Date: Nov. 18, 2004

(65) Prior Publication Data
US 2007/0091442 A1    Apr. 26, 2007

(30) Foreign Application Priority Data

May 8, 2003   (GB) .................................. 0310497.3
Jun. 19, 2003  (GB) .................................. 0314269.2

(51) Int. Cl.
*B01L 3/00*     (2006.01)
*G01N 15/14*    (2006.01)

(52) U.S. Cl.
CPC ... *B01L 3/502753* (2013.01); *B01L 3/502761* (2013.01); *B01L 2200/0647* (2013.01);
(Continued)

(58) Field of Classification Search
CPC .... G01N 30/00; G01N 15/147; G01N 1/4077; G01N 2015/144; G01N 2015/145;
(Continued)

(56) References Cited

U.S. PATENT DOCUMENTS 3,710,279 A * 1/1973 Ashkin .................... 250/281
3,808,550 A * 4/1974 Ashkin .................... 250/251
(Continued)

FOREIGN PATENT DOCUMENTS

CA    2493411     2/2004
DE    19952322    5/2001
(Continued)

OTHER PUBLICATIONS

M.P. MacDonald, G.C. Spalding and K. Dholakia; *Microfluidic Sorting in an Optical Lattice*; Nature, Nov. 27, 2003; pp. 421-424; vol. 426; 2003 Nature Publishing Group (XP-002289740).
(Continued)

*Primary Examiner* — B. Purinton
(74) *Attorney, Agent, or Firm* — Alston & Bird LLP

(57) ABSTRACT

A fractionation system comprising means for forming a three dimensional optical lattice that is operable to separate particles that have different physical characteristics. Preferably, the wells of the optical lattice are interlinked. For example, the wells may be linked in such a manner as to provide deflection greater than or equal to 15 degrees.

17 Claims, 8 Drawing Sheets

(52) U.S. Cl.
CPC .......... *B01L 2300/0864* (2013.01); *B01L 2400/0454* (2013.01); *G01N 15/1434* (2013.01); *G01N 2015/145* (2013.01); *G01N 2015/149* (2013.01)

(58) Field of Classification Search
CPC ....... G01N 30/0005; G03H 2001/0077; B01D 2015/3895; B01L 2400/0454
USPC .......................................................... 250/251
See application file for complete search history.

(56) References Cited

U.S. PATENT DOCUMENTS

| | | | |
|---|---|---|---|
| 4,523,682 A * | 6/1985 | Barmatz et al. | ............... 209/638 |
| 5,158,889 A | 10/1992 | Hirako et al. | |
| 5,245,466 A | 9/1993 | Burns et al. | |
| 5,938,904 A * | 8/1999 | Bader et al. | .................. 204/450 |
| 6,216,538 B1 * | 4/2001 | Yasuda et al. | ............... 73/570.5 |
| 6,416,190 B1 | 7/2002 | Grier et al. | |
| 6,548,124 B1 * | 4/2003 | Brumer et al. | ............... 977/887 |
| 6,833,542 B2 | 12/2004 | Wang et al. | |
| 6,974,927 B2 | 12/2005 | Hannah | |
| 7,161,140 B2 * | 1/2007 | Grier et al. | .................. 250/251 |
| 7,351,953 B2 | 4/2008 | Grier et al. | |
| 7,449,679 B2 | 11/2008 | Plewa et al. | |
| 7,612,355 B2 | 11/2009 | Wu et al. | |
| 7,732,758 B2 | 6/2010 | Dholakia et al. | |
| 8,298,727 B2 | 10/2012 | Grier | |
| RE44,711 E | 1/2014 | Wu et al. | |
| 8,816,234 B2 | 8/2014 | MacDonald et al. | |
| 2002/0160470 A1 | 10/2002 | Zhang | |
| 2002/0185592 A1 | 12/2002 | Grier et al. | |
| 2003/0007894 A1 | 1/2003 | Wang et al. | |
| 2003/0047676 A1 | 3/2003 | Grier et al. | |
| 2003/0111594 A1 | 6/2003 | Getin | |
| 2003/0132373 A1 * | 7/2003 | Curtis et al. | .................. 250/251 |
| 2004/0021949 A1 | 2/2004 | Grier et al. | |
| 2004/0067167 A1 | 4/2004 | Zhang et al. | |
| 2004/0089798 A1 | 5/2004 | Gruber et al. | |
| 2005/0247866 A1 | 11/2005 | Plewa | |
| 2006/0177940 A1 | 8/2006 | Furst | |
| 2009/0188795 A1 | 7/2009 | Oakey et al. | |
| 2010/0047761 A1 | 2/2010 | MacDonald et al. | |

FOREIGN PATENT DOCUMENTS

| | | |
|---|---|---|
| JP | 05 026799 | 2/1993 |
| WO | WO 98/10267 | 3/1998 |
| WO | WO 02/084276 | 10/2002 |
| WO | WO 03/062867 | 7/2003 |
| WO | WO 02/087792 | 11/2003 |
| WO | WO 2004/012133 | 2/2004 |
| WO | WO 2004/082840 | 9/2004 |
| WO | WO 2004/100175 | 11/2004 |
| WO | WO 2005/054818 | 6/2005 |
| WO | WO 2005/054832 | 6/2005 |
| WO | WO 2006/004558 | 1/2006 |
| WO | WO 2006/032844 | 3/2006 |
| WO | WO 2006/059084 | 6/2006 |

OTHER PUBLICATIONS

Jennifer E. Curtis, Brian A. Koss and David G. Grier; *Dynamic Holographic Optical Tweezers*; Optics Communications; Jun. 15, 2002; pp. 169-175; vol. 207; 2002 Elsevier Science B.V.
Eric R. Dufresne and David G. Grier; *Optical Tweezer Arrays and Optical Substrates Created with Diffractive Optics*; Review of Scientific Instruments; May 5, 1998; pp. 1974-1977; vol. 69, No. 5; 1998 American Institute of Physics.
J. Han and H.G. Craighead; *Separation of Long DNA Molecules in a Microfabricated Entropic Trap Array*; Science; May 12, 2000; pp. 1026-1029; vol. 288.
Dmytro Nykypanchuk, Helmut H. Strey and David A. Hoagland; *Brownian Motion of DNA Confined Within a Two-Dimensional Array*; Science; Aug. 9, 2002; pp. 987-990; vol. 297.
Deniz Ertas; *Lateral Separation of Macromolecules and Polyelectrolytes in Microlithographic Arrays*; Physical Review Letters; Feb. 16, 1998; pp. 1548-1551; vol. 80, No. 7; 1998 The American Physical Society.
T.A.J. Duke and R.H. Austin; *Microfabricated Sieve for the Continuous Sorting of Macromolecules*; Physical Review Letters; Feb. 16, 1998; pp. 1552-1555; vol. 80, No. 7; 1998 The American Physical Society.
Chia-Fu Chou, Jonas O. Tegenfeldt, Olgica Bakajin, Shirley S. Chan, Edward C. Cox, Nicholas Darnton, Thomas Duke and Robert H. Austin; *Electrodeless Dielectrophoresis of Single- and Double-Stranded DNA*; Biophysical Journal; Oct. 2002; pp. 2170-2179; vol. 83; 2002 Bighysical Society.
Pamela T. Korda, Michael B. Taylor and David G. Grier; *Kinetically Locked-In Colloidal Transport in an Array of Optical Tweezers*; Physical Review Letters; Sep. 16, 2002; pp. 128301-1-128301-4; vol. 89, No. 12; 2002 The American Physical Society.
International Search Report for PCT/GB2004/001993 dated Jul. 23, 2004.
Office Action dated Apr. 27, 2009, Canadian Application No. 2,524,646.
Office Action dated Feb. 8, 2010, Canadian Application No. 2,524,646.
Padgett, et al.; "The Angular Momentum of Light: Optical Spanners and the Rotational Frequency Shift," *Optical and Quantum Electronics*, pp. 1-12, vol. 31, No. 1, Chapman and Hall, London, Great Britain,1999.
Padgett, et al.; "Optical Tweezers and Spanners," *Physics World*, Sep. 1997, pp. 35-38, IOP Publishing, Bristol Great Britain.
Ramser, et al.; "A Microfluidic System Enabling Raman Measurements of the Oxygenation Cycle in Single Optically Trapped Red Blood Cells," *Lab on a Chip*, Feb. 21, 2005, pp. 431-436, No. 5, Royal Society of Chemistry, Cambridge, Great Britain.
International Search Reported dated Jan. 7, 2008, for application PCT/GB2007/003573, filed Sep. 20, 2007.
Office Action dated May 16, 2012, U.S. Appl. No. 12/442,327.
Office Action dated Dec. 6, 2012, U.S. Appl. No. 12/442,327.
Dharmadhikari, et al., "Torque-generating Malaria-infected Red Blood Cells in an Optical Trap," Mar. 22, 2004, vol. 12, No. 6, Optics Express, pp. 1179-1184.
Office Action dated Aug. 23, 2011, U.S. Appl. No. 12/442,325.
Office Action dated Feb. 16, 2011, U.S. Appl. No. 12/442,325.
Office Action dated Jul. 24, 2012, U.S. Appl. No. 12/442,325.
Notice of Allowance dated Dec. 24, 2012, U.S. Appl. No. 12/442,325.
Sancho, et al., "Reply" *Physical Review Letters*, May 12, 2005, Article 188902, vol. 94, The American Physical Society.
Paterson, et al., "Light-induced Cell Separation in a Tailored Optical Landscape," *Applied Physics Letters*, Sep. 13, 2005, Article 123901, vol. 87.
International Search Reported dated Apr. 23, 2008, Application No. PCT/GB2007/003578, filed Sep. 20, 2007.
United States Patent and Trademark Office, Office Action for U.S. Appl. No. 12/442,325, dated Feb. 7, 2014, 12 pages, USA.
United States Patent and Trademark Office, Notice of Allowance and Fee(s) Due for U.S. Appl. No. 12/442,327, dated Nov. 6, 2014, 14 pages, USA.

* cited by examiner

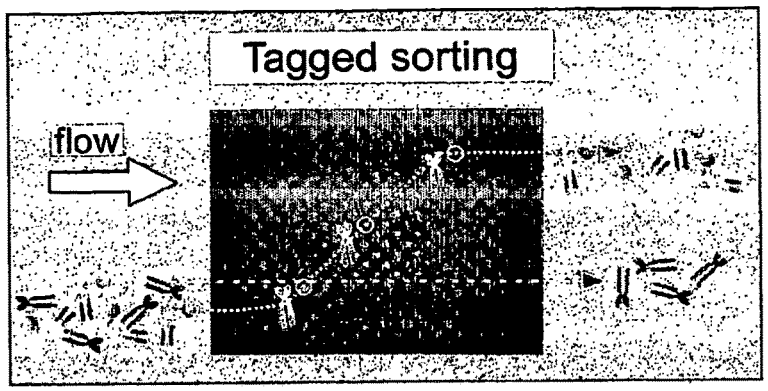
Fig.7
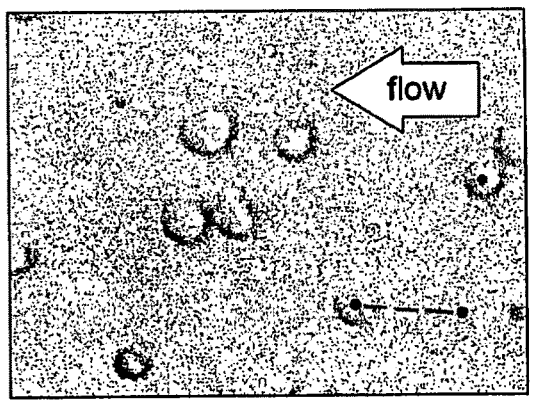
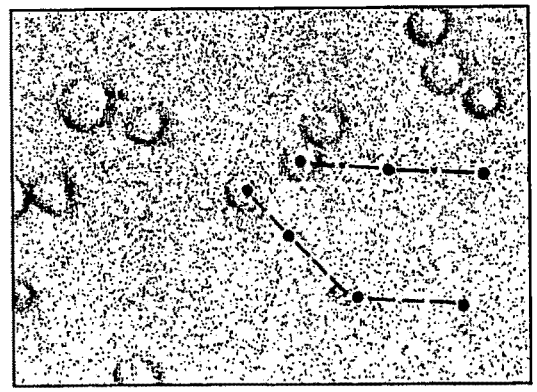
Fig.8
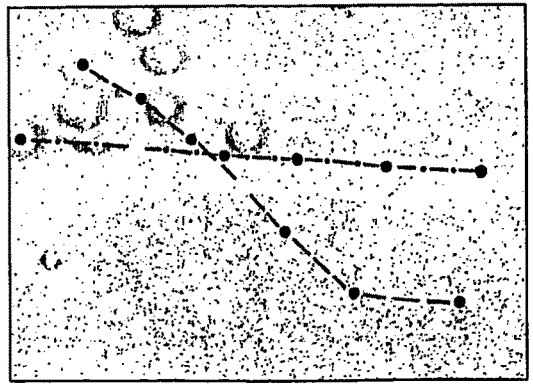
—·—·— example lymphocytes
— — — single erythrocyte

FRACTIONATION OF PARTICLES

BACKGROUND OF THE INVENTION

1) Field of the Invention

The present invention relates to a system and method for separating or fractionating particles according to one or more physical criteria. The same system can be used to insert particles into another flow stream (a form of mixing).

2) Description of Related Art

A variety of fractionation schemes exist, ranging from gel-electrophoresis, capillary electrophoresis, and analytical centrifuging to novel, entropic barriers. Examples of these are described by J. Han, H. G. Craighead, Science 288, 1026-1029 (May 12, 2000) and D. Nykypanchuk, H. H. Strey, D. A. Hoagland, Science 297, 987-990 (Aug. 9, 2002). The majority of these known techniques separate a polydisperse mixture into bands containing particles that travel at different velocities along the direction of flow. This typically leads to batch processing. In electrophoresis a gel may be used to obtain a size-dependent mobility. Recovery of fractions is achieved through post-processing of the gel. However, despite its widespread use and effectiveness this methodology is slow and importantly, due to limited pore sizes, has difficulty in separating objects at the microscopic size level, for example cells, chromosomes, and colloidal matter.

Lithographically fabricated two-dimensional, asymmetric artificial gels are also used. Examples of these are described in the articles by D. Ertas, Physical Review Letters 80, 1548-1551 (Feb. 16, 1998); T. A. J. Duke, R. H. Austin, Physical Review Letters 80, 1552-1555 (Feb. 16, 1998) and C. F. Chou et al., Biophysical Journal 83, 2170-2179 (October, 2002). These gels yield separation transverse to the direction of flow. Because of this, they can be operated in a continuous fashion, with various fractions taken up by separate collection channels. However, sorting based on diffusion becomes impractically slow at the microscopic scale and above.

Another fractionation scheme that has been proposed is described in the article "Kinetically Locked-in Colloidal Transport in an Array of Optical Tweezers" by Korda et al, Physical Review Letters, Vol 89, Number 12, 16 September 2002. In this case, a monolayer of colloidal spheres is allowed to flow through an array of discrete optical traps. By varying the orientation of the trap lattice it was shown that the direction of flow of the spheres could be varied. Because of this, it was suggested that the lattice could be used to continuously fractionate mesoscopic particles. However, because of the use of a lattice of localized discrete traps, the observed kinetically locked-in channeling along low-index lattice vectors was intrinsically limited to small-angle deflections. In practice, this limits the practicality of the lattice for use in fractionation.

Fractionation systems are used in many different applications. One field where their use is becoming of increasing interest is that of microfluidics. In microfluidics, flow is predominantly laminar, creating challenges in the design of actuators such as mixers and sorters. The ability to select and sort both colloidal and biological matter in a manner related to its physical properties in a fast and efficient manner is a key requirement at this level.

BRIEF SUMMARY OF THE INVENTION

An object of the present invention is to provide an improved system and method for separating or fractionating particles.

According to one aspect of the invention, there is provided a fractionation system comprising means for forming an optical lattice having a plurality of linked potential wells.

Preferably, the potential wells are linked in such a manner that the lattice is asymmetric. By this it is meant that the lattice has stronger connectivity along one direction than along another direction. This allows deflection in a single direction, which is a key requirement for useful deflection.

The wells in one lattice direction may be strongly linked and wells in another direction may be substantially unlinked. By strongly linked it is meant that the light intensity pattern in the said one lattice direction has peaks and troughs, wherein the intensity in a trough does not dip below approximately one third of the intensity at a peak.

Alternatively, wells in one lattice direction may be completely linked and wells in another direction may be substantially unlinked. By completely linked it is meant that there are substantially no troughs in the intensity pattern in the said one lattice direction. An advantage of this is that the problem of jamming due to localization of particles at intensity maxima can be avoided.

The wells may be linked to make possible a deflection in a range of 0 degrees to 85 degrees. The deflection angle may be 45 degrees of more.

According to another aspect of the invention, there is provided a fractionation system comprising means for forming a three dimensional optical lattice. By optical lattice is meant an intensity-modulated extended light pattern.

By providing a three dimensional optical lattice that is defined by radiation of an appropriate wavelength, particles that are incident on the lattice can be deflected by an angular amount or in a direction that depends on the physical characteristics of those particles. This is because particles having different characteristics are deflected by different amounts or in different directions. Since the lattice is three dimensional, the throughput of the system is relatively high. In this way, there is provided a very simple and effective system for effecting particle fractionation.

Preferably, the optical lattice has a plurality of linked potential wells. The wells may be linked in such a manner as to provide a deflection of 45 degrees or more According to yet another aspect of the invention, there is provided a method for optimizing fractionation of particles comprising tuning an optical lattice, preferably a three dimensional optical lattice, and/or varying particle flow rate through the lattice until optimum conditions are reached. By tuning the optical lattice it is meant varying characteristics of the beams that are used to define the lattice, such as beam intensity or lattice constant.

According to yet another aspect of the invention, there is provided a method for fractionating particles comprising forming an optical lattice that has a plurality of linked potential wells and is defined so as to cause deflection of particles as a function of a pre-determined characteristic, such as size or refractive index or shape, and causing relative movement between a fluid that contains the particles that are to be separated and the lattice. Preferably, the method involves causing a fluid flow through the lattice. Alternatively, the method may involve scanning the lattice through the fluid.

BRIEF DESCRIPTION OF THE SEVERAL VIEWS OF THE DRAWINGS

Various aspects of the present invention will now be described by way of example only and with reference to the accompanying drawings, of which:

FIG. 7 is a diagram illustrating tagged sorting, and

FIG. 8 is a view showing the separation of a single erythrocyte from a flow of lymphocytes.

DETAILED DESCRIPTION OF THE INVENTION

Figure 1:
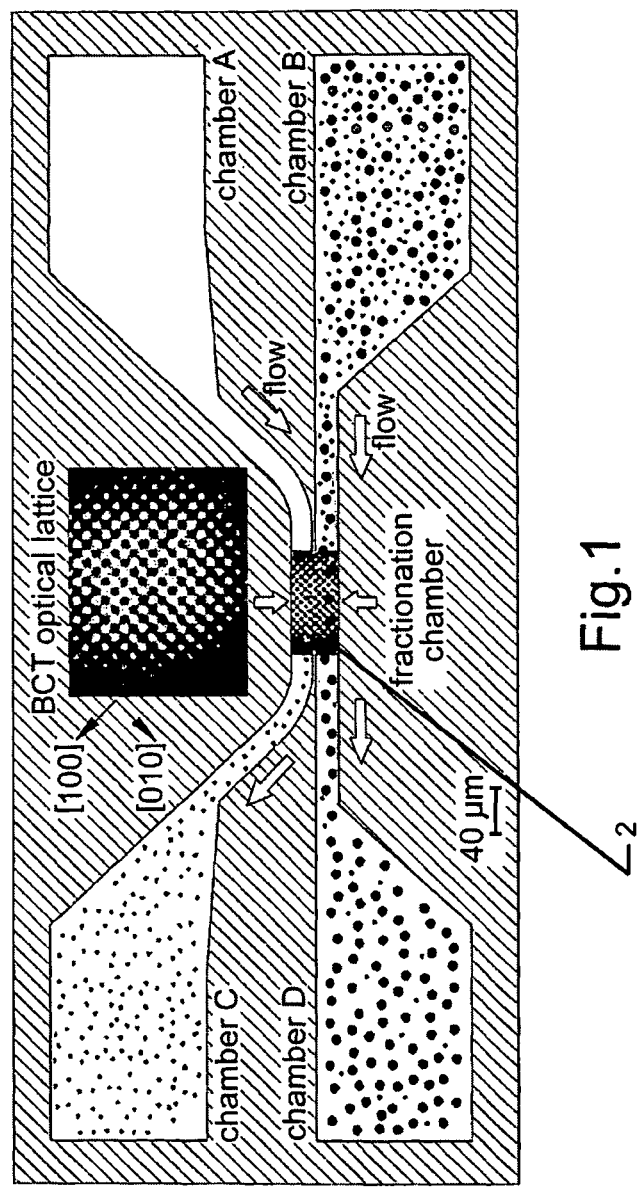
FIG. 1 is a block diagram of a system for fractionating particles using an optical lattice.

FIG. 1 shows a micro-fluidic system for fractionating particles. This has a fractionation chamber 2 and means (not shown) for defining an optical lattice within that chamber 2. Connected to the fractionation chamber 2 by suitable fluid passages are four chambers A, B, C and D. Fluid can flow between chamber A and chambers C and D via the fractionation chamber. Likewise, fluid can flow between chamber B and chambers C and D via the fractionation chamber 2. Included in chamber B is a poly-disperse fluid that includes two different particle types. Chamber A would typically introduce a "blank" flowstream, though this could be any stream into which the selected particles are to be introduced.

The optical lattice is created using a multi-beam interference pattern that forms a tailored 3D potential energy landscape, which causes micro-objects to be deflected in a desired manner. Preferably, the optical lattice is three dimensional in nature allowing the ability to sort particles throughout a three-dimensional flow. The interaction between the optical lattice and matter causes selected particle types to follow described paths through the lattice, thereby providing optical fractionation. In the example shown in FIG. 1, the optical lattice is adapted to direct one set of the particles that originate from chamber B into chamber C and the other particles into chamber D. In this case one set of particles is deflected by the optical lattice, whereas the other set is largely unaffected. It should be noted that the optical lattice, which is a modulated pattern of light, is not limited to the visible wavelengths of light.

Figure 2:
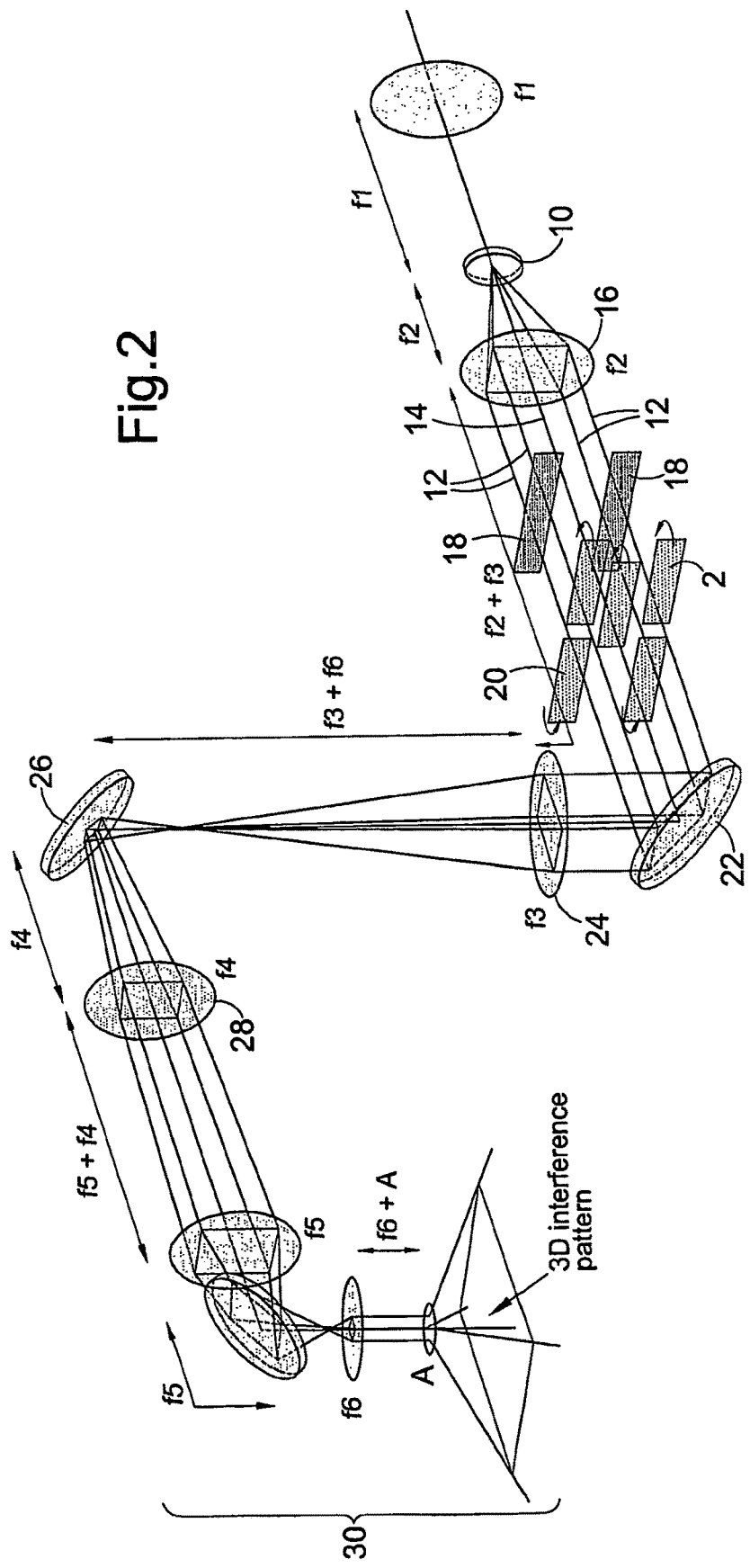
FIG. 2 is a schematic diagram of a system for defining an optical lattice in the system of FIG. 1.

Arrangements for defining optical lattices are known, and have been used for other applications. A specific example of a suitable arrangement is shown in FIG. 2. This has a diffractive-optic (DOE) beamsplitter 10 that splits a laser beam into four first-order beams 12 plus the remaining zero-order beam 14 in the centre of a cross shape. An aperture is provided to remove higher order beams. Light from the DOE 10 is directed into a first lens 16. This is positioned so that its output comprises five parallel beams, that is the four first order beams 12 and the single zero order beam 14. In the optical path of the first order beams are provided neutral density filters 18. These reduce the intensity of the first-order beams so that stronger linkage between intensity maxima of the multi-beam interference pattern can be obtained. As a specific example the neutral density filters 18 may each have a power of 0.3D.

Downstream from the neutral density filters 18 are coverslip slivers 20, which can be used to change the effective path length of a beam without introducing significant deflection. On the optical path from the coverslips 20 is a mirror 22 that turns the light about ninety degrees onto another lens 24, which focuses the light towards another mirror 26. Light reflected from the mirror 26 is directed towards another lens 28, which is positioned so as to provide an input having four parallel first order beams and a zeroth order beam to an optical tweezer arrangement 30. Optical tweezer arrangements are generally adapted to hold particles within potential wells. However, for the purposes of the present invention, trapping of particles is undesirable. Hence, although an optical tweezer arrangement 30 can be used to define a lattice of discrete sites, here it is adapted so that optical gradient forces and/or radiation pressure can be effective to deflect particles moving through an extended lattice. There is no need for optical tweezing, per se, i.e. there is no need to retain particles within the optical wells. Hence, the lattice that is used is not an array of optical tweezers. Using the arrangement of FIG. 2, it is possible to generate a 3D optical lattice, in particular a body-centred tetragonal lattice, using a five-beam interference pattern. When a flow of mixed particles is passed through the lattice, selected particles are strongly deflected from their original trajectories while others pass straight through largely unhindered, depending crucially upon their sensitivity to the optical potential.

The fractionation system of FIG. 1 is based on the fact that a particle can be deflected when it moves within an optical lattice, because of the spatial variation of the radiation field. The energy reduction, U, which occurs when a dielectric particle sits at particular point in the optical lattice, (as opposed to a point far outside of the laser beam) can be found by integrating the product of the relative polarizability and the local energy density, $\eta$, over the volume V of the particle:

$$U = \frac{\varepsilon - \varepsilon_0}{\varepsilon_0} \int \eta dV \tag{1}$$

It should be noted that this does not take into account all of the complicating factors present, notably radiation pressure. However, it serves as a reasonable guide over a wide range of particle sizes, allowing insight into the various flow regimes available to this system, as well as identification of the primary control parameters.

From Equation (1), it can be seen that the local trapping potential is a function of the polarizability of the particle material as compared to that of the surrounding medium, the local intensity of the lattice and particle size. For small particles, up to the scale of the intensity maxima of a given lattice site in the optical lattice, the interaction grows as the third power of the radius allowing for fractionation of particles by size. For larger particles, the interaction strength depends upon the specific relation of the particle size to the lattice parameters of the optical lattice. Alternatively, the lattice parameters can be tuned to remove any size dependence (over some range of particle sizes), thereby allowing selection based purely on index of refraction. This sort of tunable selection criteria is a key feature of the method. For guiding it is important to consider the difference in potential between adjacent lattice sites, i.e. $\Delta U$, as the particle moves through the optical lattice from a maximum to a minimum in the light intensity. The larger the trapping potential is the greater will be the force exerted on a particle. However, the fluid flowing through the optical lattice exerts a Stoke's drag on the particles within that flow acting in the direction of the flow. The Stoke's drag exerts a force on the particle given simply by Stoke's law (for spherical particles), equal to the force required in order to hold a particle against the flow:

$$F=6\pi\eta rv \quad (2)$$

Where $\eta$ is the viscosity of the fluid containing the particles r is the radius of the particle and v is the velocity of the fluid flow. If the forces exerted on a particle by an intensity maximum in the lattice (optical forces, particularly the gradient force) are greater than the Stoke's force, then particles will simply stick in the lattice and the system will become clogged. In the opposite extreme, if the optical forces are much smaller than the Stoke's force then a particle will pass through the optical lattice unhindered. By tuning between the two extremes of a clogged lattice and free flow, it is possible to get deflection of particles flowing through the lattice. This regime exists close to the point at which jamming occurs, such that particles are able to hop between intensity maxima such that they get guided diagonally across the flow. Because this regime exists at a different flow velocity/lattice power for particles with different polarisabilities, it is possible to obtain selective guiding and hence sorting of particles. For guiding it is important to consider the difference in potential between adjacent lattice sites, i.e. $\Delta U$, as the particle moves through the optical lattice from a maximum to a minimum in the light intensity. With a lower barrier height, transport between adjacent lattice sites is enhanced due to the lowered barrier providing a preferential exit direction for a particle at a local intensity maximum.

To improve separation efficiency, a high deflection angle is desirable. In order to allow this, some degree of optical connectivity between adjacent nodes of the lattice is important. By this is meant that the potential wells are not separated in all directions by high barriers. To achieve this, the distribution of light intensity is sculpted accordingly. In this way, barrier heights can easily be reduced along one direction with respect to another by tuning the relative intensity or phase of the beams forming the lattice.

Figure 3:
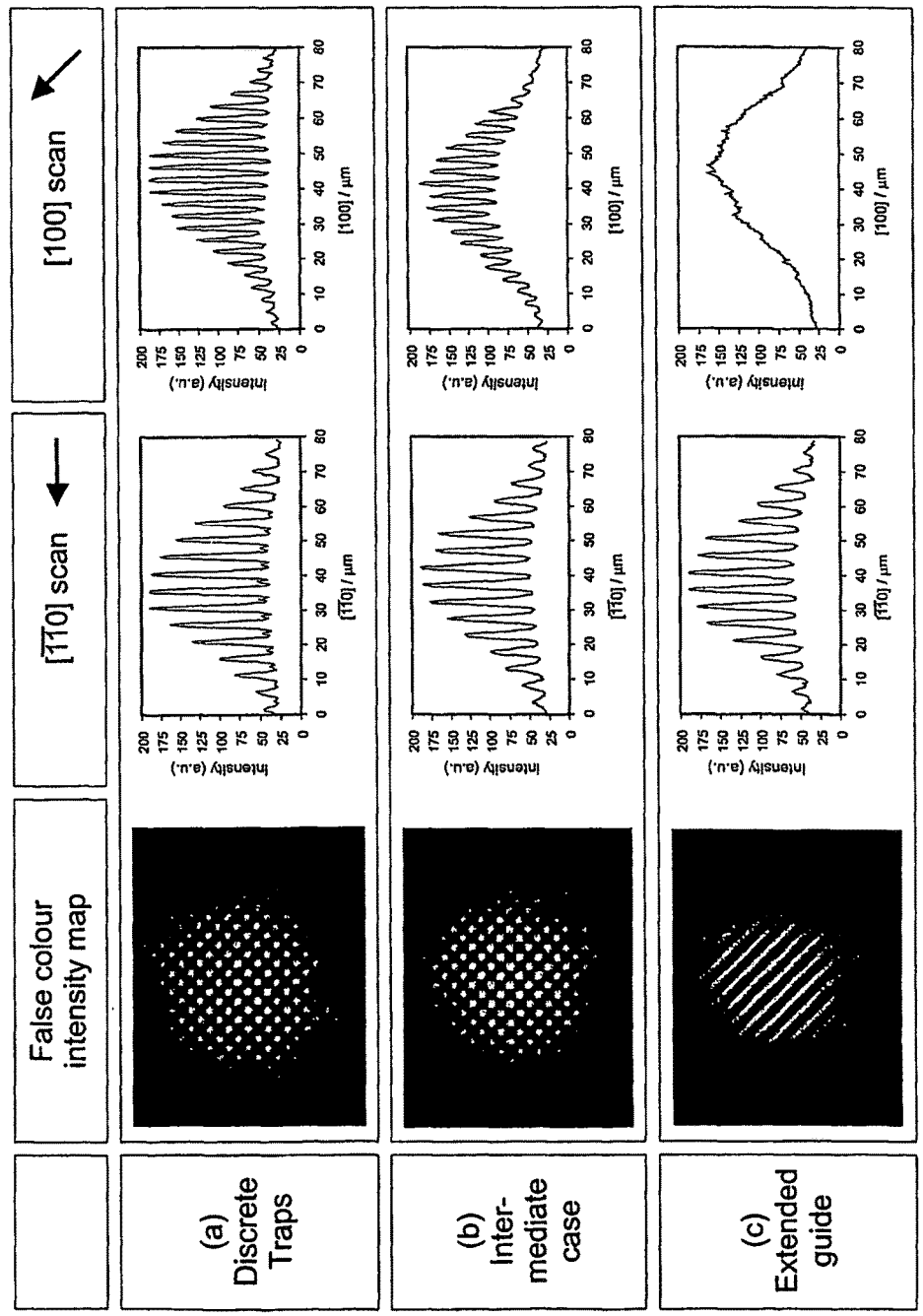
FIG. 3(a) is a false-colour intensity map and two scans for an optical lattice in which discrete traps are defined.
FIG. 3(b) is a false-colour intensity map and two scans for an optical lattice in which weakly linked traps are defined.
FIG. 3(c) is a false-colour intensity map and two scans for an optical lattice in which extended guides are defined.

FIG. 3 shows various false-colour intensity maps and intensity line scans for optical lattices that have different barrier heights between the lattice maxima. In particular, FIG. 3(a) shows a lattice in which the interference maxima have equal intensity in the zeroth-order and total first-order, giving discrete, well-separated intensity maxima, almost completely unlinked in any direction. FIG. 3(b) shows an intensity map and two line scans for the situation where a neutral density filter of 3D is used on the first-order beams to introduce strong linkage along the [100] direction, whilst maintaining strong isolation along the [110] direction. Hence, the lattice used is asymmetric, that is there is stronger connectivity along one diagonal than along the opposite diagonal. FIG. 3(c) shows an intensity map and two line scans for the situation where two diagonally opposite first-order beams are completely removed to yield complete linkage along the [100] direction while, again, maintaining isolation along the [110] direction. These fringes also exist along the z-axis, such that the line maxima, that is rods of high intensity, lie in a log-pile formation, so that they form a triangular lattice of extended optical guides. Again, this results in an asymmetric lattice, but in this case, there is no linkage in one direction and complete linkage in the other, thought this might not be the case for all situations. In practice, optimal performance can be found with the pattern shown in FIG. 3(b). This balances the need for strong interaction—which favours discrete trap lattices (FIG. 3a)—with the need for strong (high-angle) lateral deflection—which favours a lattice of extended lines of laser light or light fringes (FIG. 3c).

Figure 4:
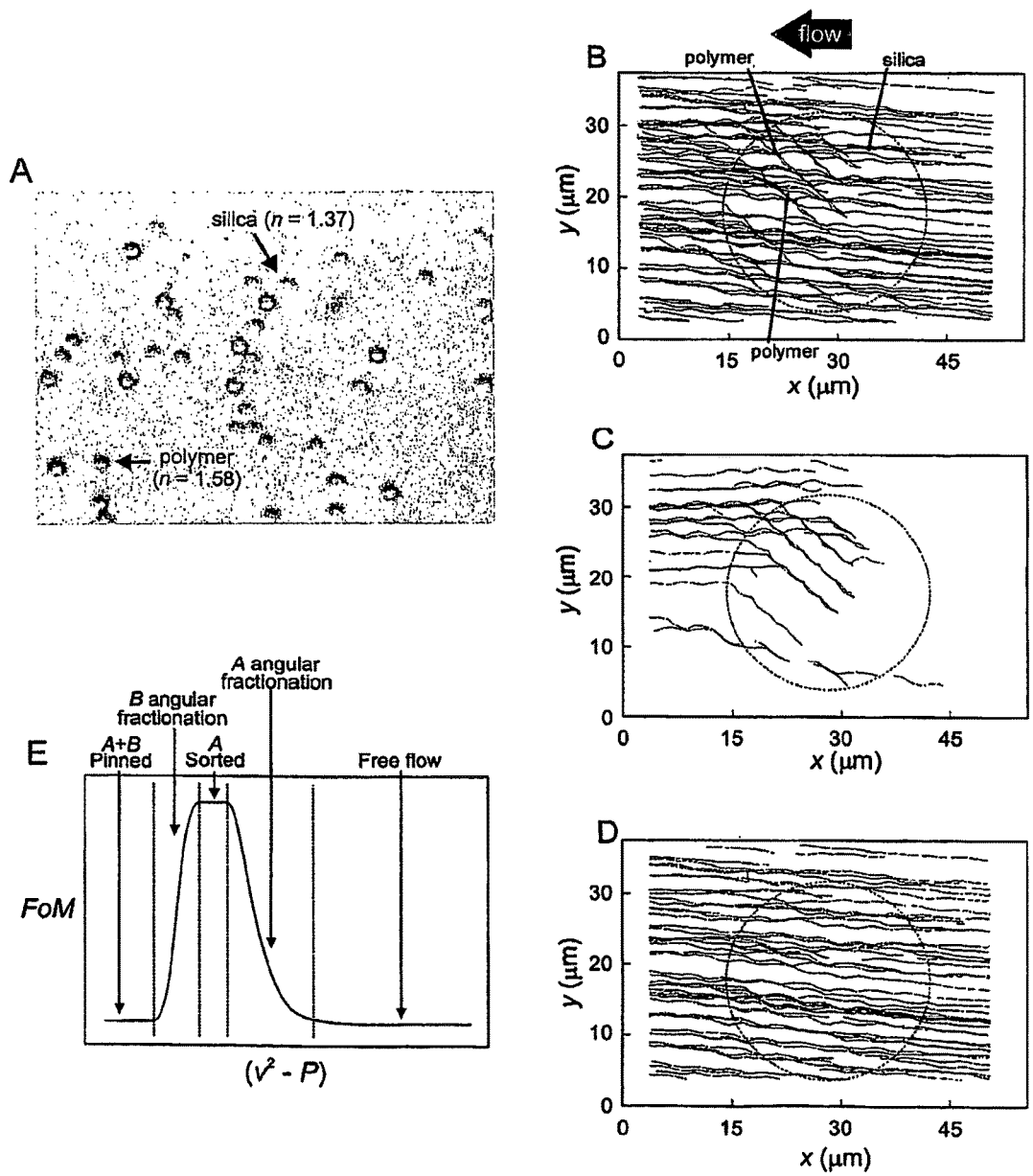
FIG. 4(a) is a view of a silica/polymer mix.
FIG. 4(b) is view of the trajectories traced by the particles of the mix of FIG. 4(a) as they move through a three dimensional optical lattice.
FIG. 4(c) is a separate view of the trajectory for the polymer.
FIG. 4(d) is a separate view of the trajectory for the silica.
FIG. 4(e) indicates that the throughput can be increased without cost to efficiency by increasing the laser power as flow speed is increased.

Using the arrangement of FIG. 1, different particles can be separated according to various physical criteria. For example, particles of the same size, but different polarizabilities (or, equivalently, refractive indexes) can be separated by selecting an appropriate lattice. FIG. 4 shows polymer and silica spheres co-flowing from right to left through a body-centered tetragonal optical lattice. The size of the silica and polymer spheres is the same, (and hence their Stoke's force is the same), but the optical forces exerted upon a polymer sphere is greater, due to its higher relative polarisability. The fluid speed was 30 μm/s, with a total incident laser power of 530 mW. In this example, the optical lattice was such that there was a stronger linkage between intensity maxima along the [100] direction than those along the [010] direction. This linkage encourages selected particles to follow the [100] direction instead of the [010] direction, as less force is required to move a particle between intensity peaks in the [100] direction.

FIG. 4(a) is an image of the silica/polymer mix, indicating the typical particle density. In this example, the polymer has a relatively lower density than the silica. Differences in contrast allow each particle to be tracked separately using particle image velocimetry. FIG. 4(b) shows various trajectories for the mix of FIG. 4(a), with a circle indicating the xy range over which the optical lattice is most intense. From this it can be seen that co-flowing particles can be separated using the optical lattice. The estimated throughput of the system was about 25 particles per second. For the sake of clarity, the trajectories for the polymer and silica are shown separately in FIGS. 4(c) and 4(d) respectively.

From FIG. 4(c), it can be seen that the polymer tracks show a deflection of approximately 45 degrees. This very large angular separation can be attributed to the linking of intensity maxima along the [100] direction of the optical lattice. In this case, the polymer spheres nearly all enter the field of view only once they reach the strongest part of the optical lattice. The lower density of the polymer spheres means that they normally flow away from the bottom surface of the sample cell, but are subsequently guided into the focal plane of monitoring optics by the optical forces. Once in the focal plane, all of the polymer spheres move along the [100] direction, and none along the [010]. This is due to an asymmetry introduced between the <100> directions of the underlying optical lattice. In contrast, as shown in FIG. 4(d) the silica tracks are only slightly modulated by the optical lattice. In this case, the silica spheres all enter the field of view at the right edge and move in approximately straight lines, except in the mid-left portion of the field of view, where they are deflected to and fro (slightly) by the strongest part of the lattice, with no net deflection resulting. Hence, it can be seen that the silica and polymer spheres can be separated, because of the differences in the polarisabilities of the two materials, which causes the spheres to interact with the lattice in different ways.

FIG. 4(e) indicates that the throughput can be increased without cost to efficiency by increasing the laser power (and hence ΔU) as flow speed is increased. For any given laser power, as the particle flow speed is increased or laser power is decreased or particle size or relative polarizability is changed, a crossover is observed from strongly trapped to hopping behaviour to guided flow. This can be further tuned from pseudo-ballistic to diffusively guided regimes, and—finally—to the limit where all particles flow past unhindered. A spread in angular deflections (fractionation) results for any suspension containing a broad distribution of sizes. Further, as particle-particle interactions become significant (either as a function of screening length or density), the de-pinning transition can take on a collective, many-body character. At speeds just beyond de-pinning, both species are deflected by the optical lattice. By appropriately selecting the particle speeds/laser power optimal separation can be achieved.

Figure 5:
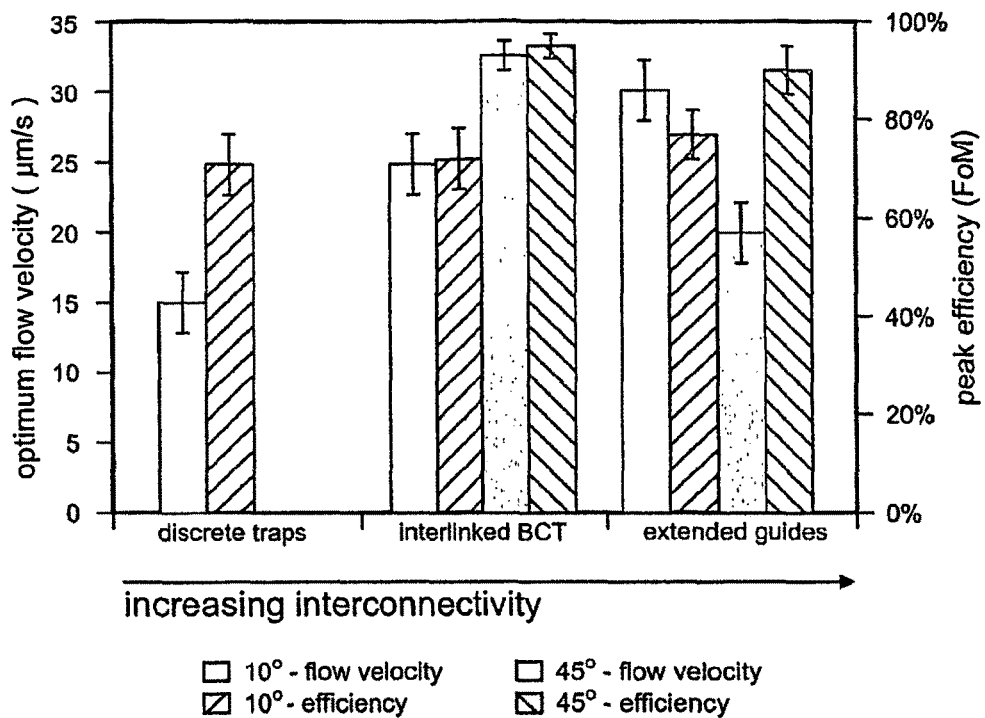
FIG. 5 is a plot showing experimental results for various different lattice types.

In order to compare the effects of using different lattice types, various experiments have been done. In each case a mixed flow of 2 micron silica and 2 micron polymer spheres were fractionated due to their differing refractive indices. The total laser power in the lattice was kept the same between experiments at equal angles (2 W at 45 degrees and 0.75 W at 10 degrees) as were all other parameters. The results are shown in FIG. 5. From this, it is clearly seen that for sorting at 45 degrees optimal performance comes through use of the linked lattice of FIG. 3(b), which is a body centred tetragonal lattice (BCT). At 10 degrees, where the discrete lattice sites are capable of particle deflection, the extended guides give the highest flow velocity, but the BCT lattice has a lower error rate with no particles of species B being deflected above 10 microns/s. It is noticeable that in a situation where large angle deflections are not critical it is possible to operate at much lower laser powers for the same flow velocity. However use of such lower angles requires longer lattices and increases the probability of many-body effects reducing the performance of the system. In the case of the discrete traps, it was found that this lattice is incapable of fractionation at 45 degrees, represented as an optimum velocity of 0 micron/s and that it is also less effective compared to the other lattices at lower angles of deflection. All these results were obtained from quantitative experiments of the type shown in FIG. 4.

Figure 6:
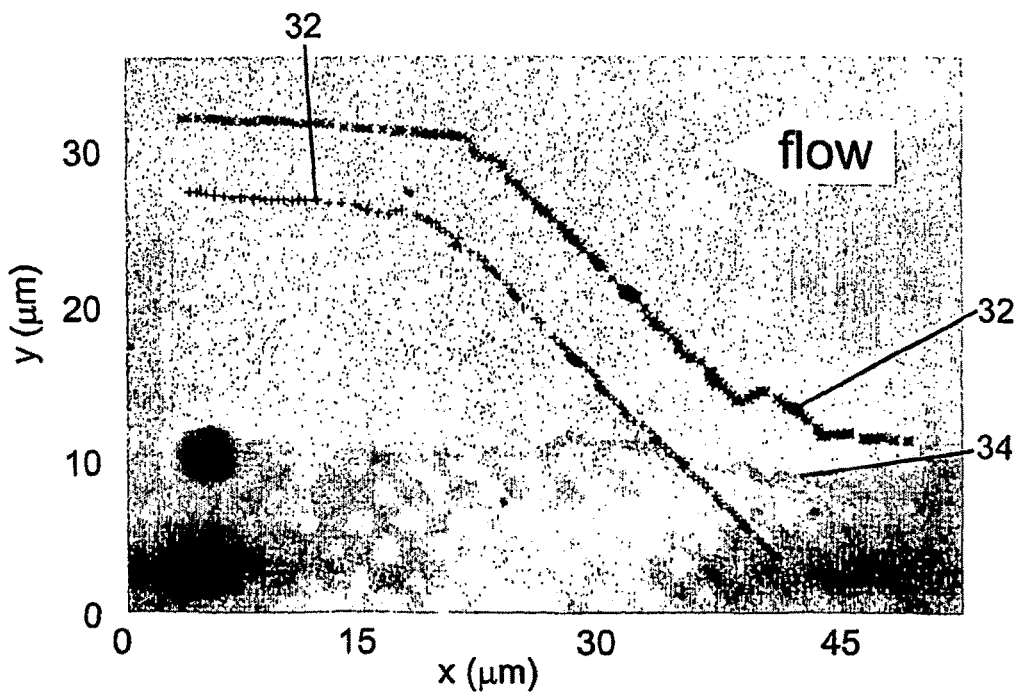
FIG. 6 is view of the trajectories traced by the particles of another poly disperse mix as they move through a three dimensional optical lattice.

Particles can also be separated according to size. Separation according to size has also been demonstrated experimentally using both silica spheres and low index particles. In FIG. 6 black crosses 32 represent positions of two 2-μm diameter protein microcapsules as they flow from right to left across the optical lattice. Again, significant angular deflection is achieved, while a co-flowing 4-μm diameter capsule of the same sort flows nearly straight through, as shown by the dots 34. In this case, the flow speed is 20 μm/s with a total incident power of 530 mW. This allows the creation of a monodisperse collection of protein microcapsules. These protein microcapsules are an ultrasound contrast agent that can be used to locally permeate cell membranes. This is of interest for direct DNA transfection or drug delivery, a technique known as sonoporation. The ability to create a monodisperse collection of these protein microcapsules offers greatly enhanced control and understanding of the processes involved in sonoporation. Notably, here optical fractionation has been demonstrated for particles with a lower index of refraction than the surrounding medium.

However, as will be appreciated, although the physical mechanisms for separation are analogous to those for high-index particles, low-index particles are repelled by, rather than attracted to, regions of high light intensity.

Where there is insufficient differentiation between the polarisabilities of particle species within a mixed flow or where a particle species is too small to achieve non-resonant attraction to the optical lattice (e.g. proteins), tagged sorting can be used. In this approach, tagged helper particles are used such as streptavadin or antibody coated microspheres to select a specific particle species that can then be separated using an optical lattice. FIG. 7 shows a diagrammatic representation of this technique using chromosomes.

The methodology in which the invention is embodied is particularly useful for sorting cells and DNA. These can be sorted in the same manner as other particles, that is: by their physical properties such as size, shape or refractive index. The sorting of erythrocytes from lymphocytes is shown in FIG. 8. This shows a single erythrocyte being selectively guided through the optical lattice as the rest of the cells in the flow (lymphocytes) pass straight through unhindered. Separation of macromolecules such as DNA and proteins can take place directly in the lattice, through the use of tagged spheres as outlined above or where such tags do not exist to use one of the techniques described below (E).

The present invention provides many advantageous technical features. A key feature of the methodology is its non-invasive nature and the accompanying ability to sort particles without any physical contact in the system whatsoever. The method is reconfigurable such that its selection criteria can be tuned in real time. Furthermore, sole use of optical forces simplifies surface interaction and sterility issues by removing the extremely high surface area associated with any physical sieve or gel. Efficiency can approach 100%, with values of 96% or more observed even at the upper-limit of the semi-dilute regime. This can be achieved without the need to expose analytes to high electrical charge, and whilst avoiding the introduction of further material surfaces as would be associated with microfabricated sieves. This simplifies the lithographic requirements of the sample cells. Furthermore, the invention does not require the use of unreliable micro-constrictions, thereby reducing the likelihood of blockages or clogs. A yet further advantage is that by using an optical lattice, the need to tag particles that are to be separated can be avoided, although as described previously tagging can be used as and when desired for additional functionality. Also, there is no need for the particles to have different fluorescences. In addition unlike some existing methods, the method in which the invention is embodied enables the separation of particles that have sizes that differ by less than 20%. This increases the practicality of the technique, allowing it to be used for many different applications. Furthermore, the technique can be integrated into existing microscopes or used as a stand-alone device. It is also ideally suited to integration into other sorting techniques based on micro-flows to give complementary sorting properties or to be incorporated into a larger micro-total analysis system.

Figure 9A:
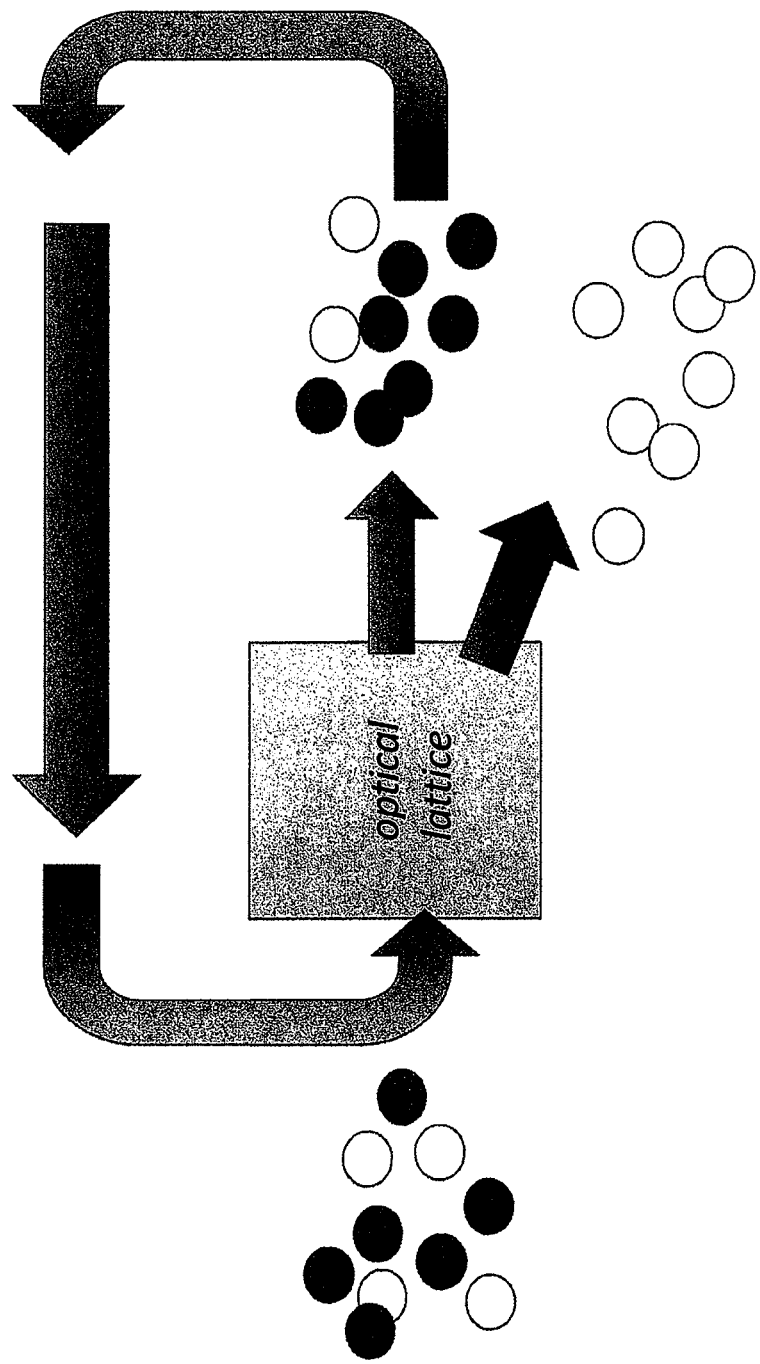
FIG. 9(a) is a schematic diagram illustrating re-circulated separation
Figure 9B:
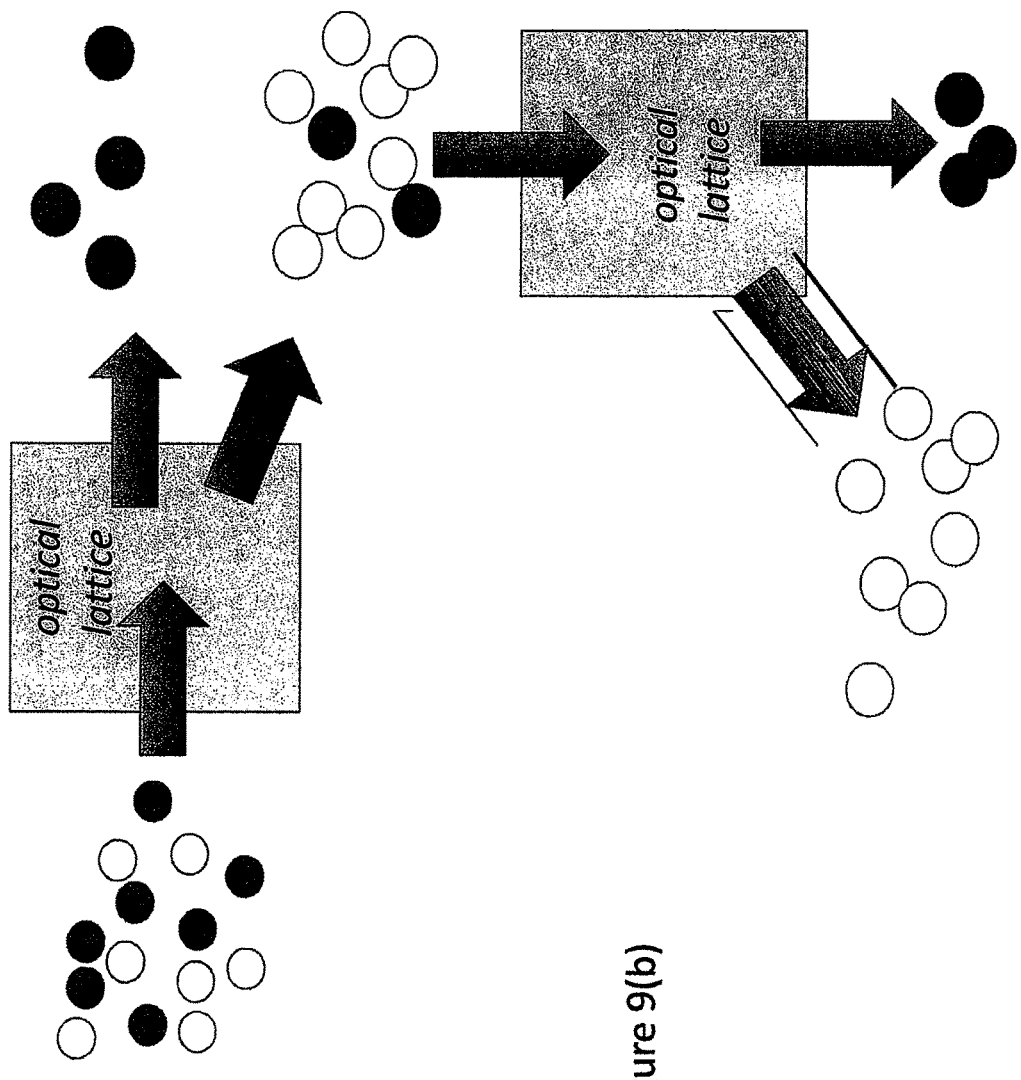
FIG. 9(b) is a schematic diagram illustrating cascaded separation

A skilled person will appreciate that variations of the disclosed arrangements are possible without departing from the invention. For example, for weakly segregated species, the analyte can be either re-circulated through the optical lattice as illustrated in FIG. 9(a) or directed through cascaded separation chambers as illustrated in FIG. 9(b). An advantage of this latter option is that it allows for the employment of multiple selection criteria in a single integrated chip. Also whilst the description has focused on sorting by size or type of particle, it is possible to use the invention to sort particles according to their shape. This is because different shapes of particles will interact more or less strongly with the optical lattice such that particles can also be sorted by shape. An example is that a cylindrical object will interact more completely (due to its aligning with the lattice) with an lattice of extended guides than a spherical particle hence making it possible to sort cylindrical particles from spherical particles.

Furthermore, the use of optical lattices can be generalised to the case of an optical landscape (an optical pattern either 2D or 3D with or without rotational or mirror symmetry). In this case it is not always necessary to have a flow through the lattice but in fact the pattern (including the optical lattice) can be scanned dynamically such that the selective movement of particles is provided by the movement of the lattice (movement and scanning in this case means not the movement of the entire pattern but rather the movement of the features of the pattern such that a particle follows for example a light maxima that travels across the area of the pattern). In this scenario, when moving the landscape itself, the movement of a particle depends critically on the relative speed of the landscape versus the Kramer's time i.e. how long the particle resides in a local intensity maximum and whether or not that time is shorter than the time for that maximum to traverse the particle. It is also possible to combine the two techniques together such that the dynamic lattice adds to functionality of the static lattice for sorting particles that flow through the optical lattice. Accordingly, the above description of the specific embodiment is made by way of example only and not for the purposes of limitation. It will be clear to the skilled person that minor modifications may be made without significant changes to the operation described.

The invention claimed is:

1. A fractionation system for separating particles that have different physical characteristics, the particles being provided in a fluid flow, the system comprising:
    at least one laser and one or more optical elements for forming a three dimensional optical lattice having a plurality of optical potential wells, each optical potential well being located at a different position in three dimensional space so that the positions of the plurality of optical potential wells define a three dimensional volume,
    wherein some of the optical potential wells are optically linked, so that the optical potential between the linked wells does not go to zero and the other optical potential wells are substantially unlinked, wherein the linked optical potential wells are linked in such a way as to provide an asymmetric three dimensional lattice;
    wherein the particles in the fluid are subject to forces generated by the optically linked potential wells and the fluid flow, and wherein the optical and fluid flow forces are configured to act together to cause deflection of some particles depending on a physical characteristic of those particles.

2. A system as claimed in claim 1 wherein the wells in one lattice direction are strongly linked and wells in another direction are substantially unlinked.

3. A fractionation system as claimed in claim 1 wherein wells in one lattice direction are completely linked and wells in another direction are substantially unlinked.

4. A system as claimed in claim 1, wherein two or more optical lattices are provided in series.

5. A system as claimed in claim 1 further comprising a fractionation chamber in which the optical lattice is defined.

6. A system as claimed in claim 5 comprising one or more capture chambers for capturing particles separated in the fractionation chamber.

7. A system as claimed in claim 1 that is operable to scan the optical lattice.

8. A fractionation system comprising at least one laser and one or more optical elements for forming a three dimensional optical lattice for separating particles that have different physical characteristics wherein the optical lattice has a plurality of optically linked potential wells, wherein the optical potential between the linked wells does not go to zero and wherein the three dimensional optical lattice is defined by a three dimensional intensity pattern.

9. A system as claimed in claim 8 wherein wells of the optical lattice are interlinked.

10. A method for optimizing fractionation of particles comprising tuning a three dimensional optical lattice or varying particle flow rate through the lattice until optimum conditions are reached, wherein the optical lattice has a plurality of optically linked potential wells defining a three dimensional intensity pattern, wherein the optical potential between the linked wells does not go to zero.

11. A method as claimed in claim 10 wherein the step of tuning involves varying a linkage between adjacent potential wells in the lattice.

12. A method for fractionating particles comprising:
    forming a three dimensional optical lattice that has a plurality of optically linked potential wells, each potential well being located at a different position in three dimensional space so that the positions of the plurality of potential wells define a three dimensional volume, wherein the optical potential between the linked wells does not go to zero; and
    causing relative movement between a fluid that contains the particles that are to be separated and the lattice,
    wherein the particles in the fluid are subject to forces generated by the optically linked potential wells and the relative movement of the fluid, and wherein the optical and relative movement forces are configured to act together to cause deflection of some particles depending on a physical characteristic of those particles.

13. A method as claimed in claim 12 comprising causing a fluid flow through the lattice.

14. A method as claimed in claim 12 comprising scanning the lattice through the fluid.

15. A collection of particles/cells separated using the system of claim 1.

16. A system as claimed in claim 1, wherein the system is adapted to re-circulate the fluid through the optical lattice.

17. The system as claimed in claim 1, wherein the linked potential wells define a three dimensional path that at least in part defines a preferential three dimensional exit direction.

* * * * *